(12) United States Patent
Tieu et al.

(10) Patent No.: US 7,628,797 B2
(45) Date of Patent: Dec. 8, 2009

(54) SYSTEM, APPARATUS, AND METHOD FOR FASTENING TISSUE

(75) Inventors: Tai Tieu, Fountain Valley, CA (US); Joshua Benjamin, Costa Mesa, CA (US); David Zarbatany, Laguna Niguel, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 561 days.

(21) Appl. No.: 11/345,208

(22) Filed: Jan. 31, 2006

(65) Prior Publication Data

US 2007/0179530 A1 Aug. 2, 2007

(51) Int. Cl.
*A61B 17/04* (2006.01)
(52) U.S. Cl. ............. 606/148; 606/232; 24/129 R
(58) Field of Classification Search ............. 606/148, 606/232, 151, 157; 24/115 H, 129 B
See application file for complete search history.

(56) References Cited

U.S. PATENT DOCUMENTS

| | | | |
|---|---|---|---|
| 5,330,442 A | 7/1994 | Green et al. | |
| 5,567,074 A * | 10/1996 | Dovak et al. | 403/197 |
| 5,609,598 A | 3/1997 | Laufer et al. | |
| 5,643,289 A | 7/1997 | Sauer et al. | |
| 5,695,504 A | 12/1997 | Gifford et al. | |
| 5,713,911 A | 2/1998 | Racenet et al. | |
| 5,769,863 A | 6/1998 | Garrison | |
| 5,849,019 A | 12/1998 | Yoon | |
| 5,976,159 A | 11/1999 | Bolduc et al. | |
| 6,015,417 A | 1/2000 | Reynolds, Jr. | |
| 6,088,889 A | 7/2000 | Luther et al. | |
| 6,165,204 A | 12/2000 | Levinson et al. | |
| 6,210,419 B1 | 4/2001 | Mayenberger et al. | |
| 6,626,930 B1 | 9/2003 | Allen et al. | |
| 6,641,592 B1 | 11/2003 | Sauer et al. | |
| 6,860,890 B2 | 3/2005 | Bachman et al. | |
| 7,083,628 B2 | 8/2006 | Bachman | |
| 7,094,244 B2 | 8/2006 | Schreck | |
| 2003/0167062 A1 | 9/2003 | Gambale et al. | |

(Continued)

FOREIGN PATENT DOCUMENTS

| | | |
|---|---|---|
| WO | WO 00/59382 | 10/2000 |
| WO | WO 2005/110244 | 11/2005 |

OTHER PUBLICATIONS

International Search Report for Patent Application No. PCT/US2007/001273, Filed Jan. 19, 2007.

*Primary Examiner*—(Jackie) Tan-Uyen T Ho
*Assistant Examiner*—Alexander Orkin
(74) *Attorney, Agent, or Firm*—David L. Hauser

(57) ABSTRACT

A clip for securing suture includes a generally tubular body, with one or more tabs cut from the wall of the generally tubular. The tab in an open configuration has the tabs in general alignment with the tab out wall, and the tab in a closed configuration has the tabs bent or otherwise positioned to extend into and at least partially obstruct the inner lumen. The tab may be formed as a generally horse-shoe shaped cut out, and may include a generally elliptical portion having a width and length. The tab may have a width generally the same size as the diameter of the inner lumen. The clip can be formed from memory material such as nitinol, and the clip may be biased toward its closed configuration.

17 Claims, 13 Drawing Sheets

U.S. PATENT DOCUMENTS

| | | |
|---|---|---|
| 2003/0167071 A1 | 9/2003 | Martin |
| 2004/0068272 A1 | 4/2004 | Sauer et al. |
| 2004/0097978 A1* | 5/2004 | Modesitt et al. ............. 606/148 |
| 2004/0181238 A1 | 9/2004 | Zarbatany et al. |
| 2005/0251209 A1* | 11/2005 | Saadat et al. ................ 606/232 |
| 2006/0004410 A1 | 1/2006 | Nobis et al. |
| 2006/0167338 A1 | 7/2006 | Shfaram |

* cited by examiner

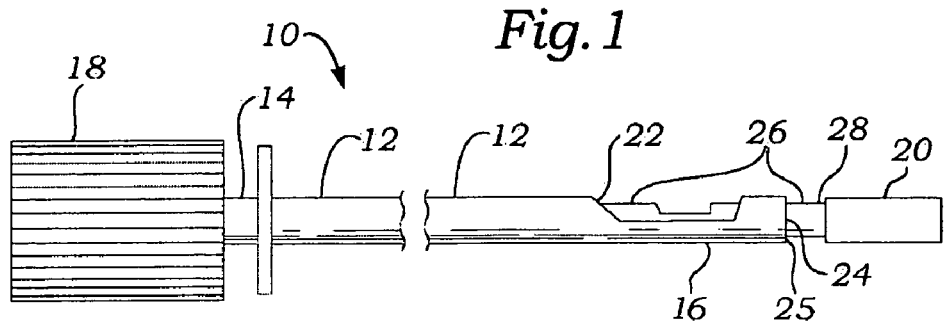
Fig. 1
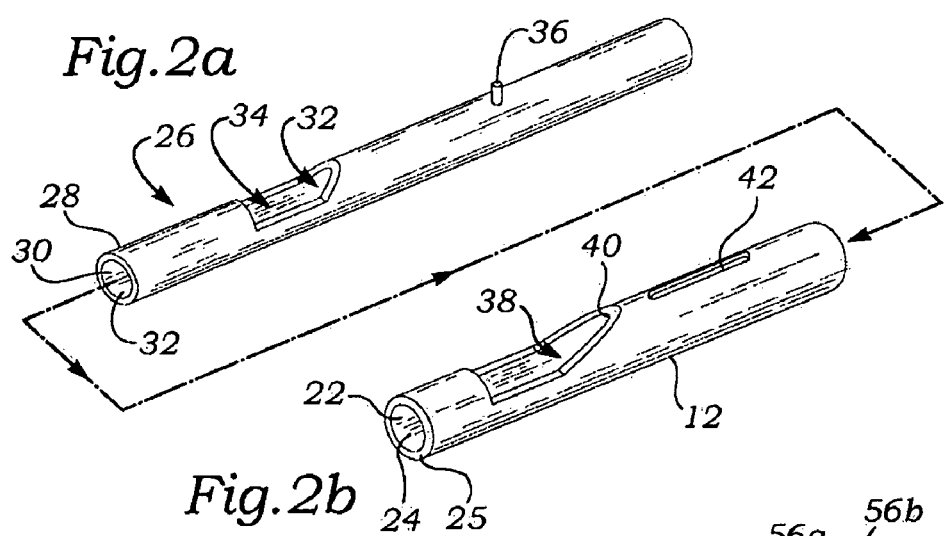
Fig. 2a
Fig. 2b
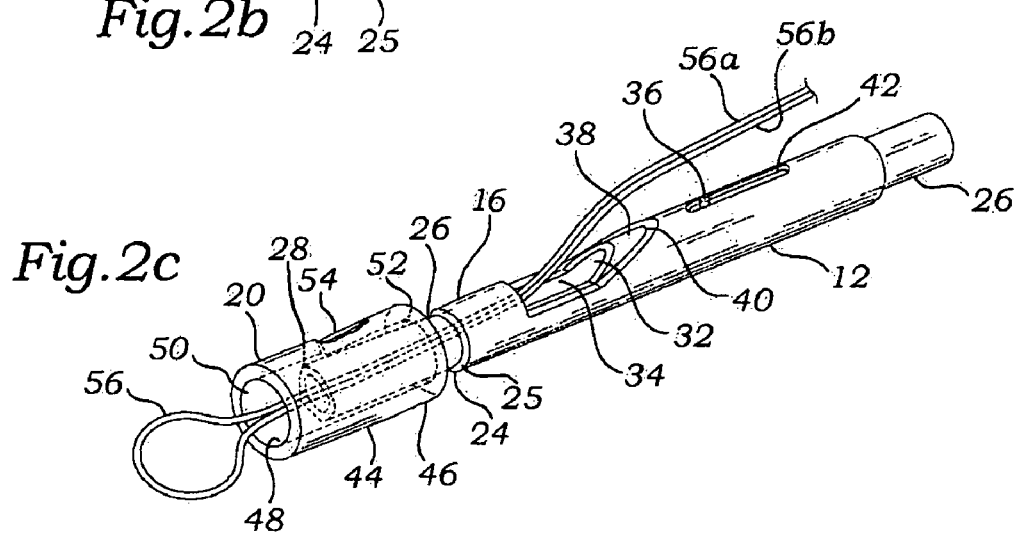
Fig. 2c

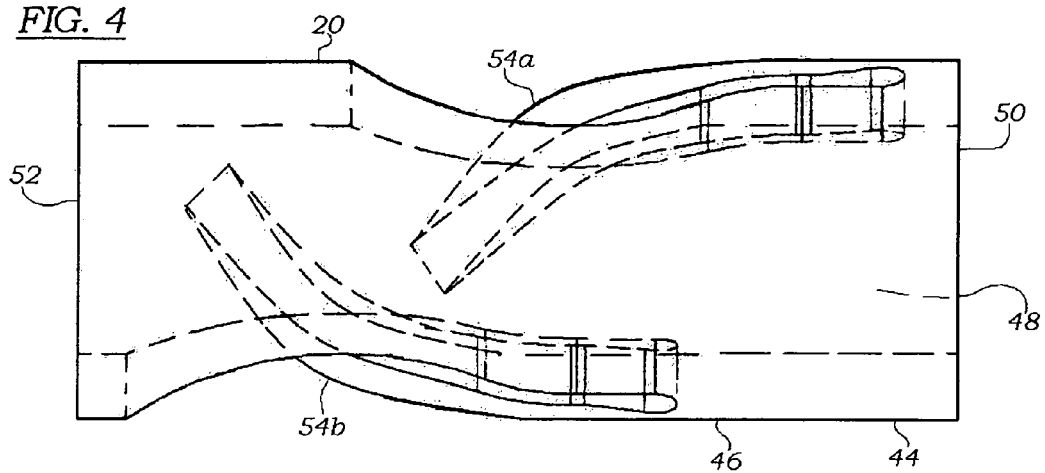
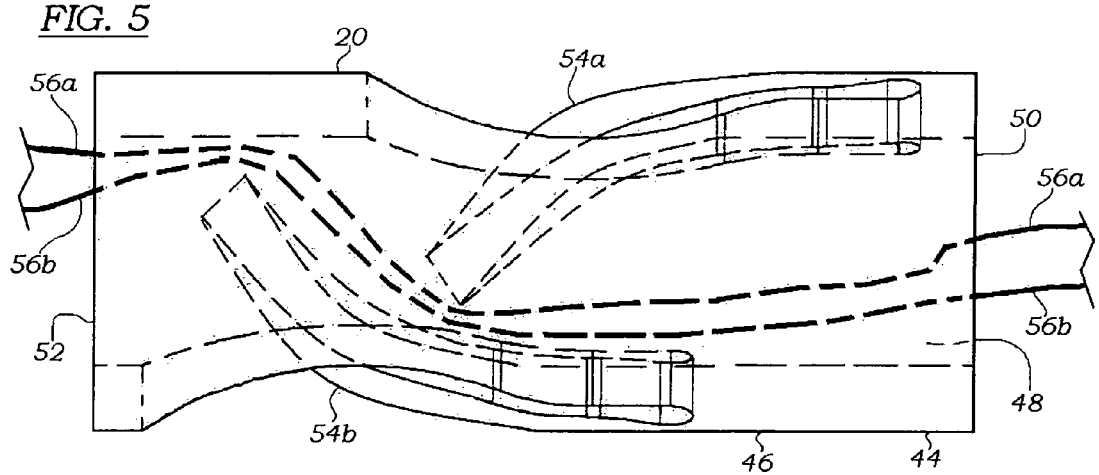

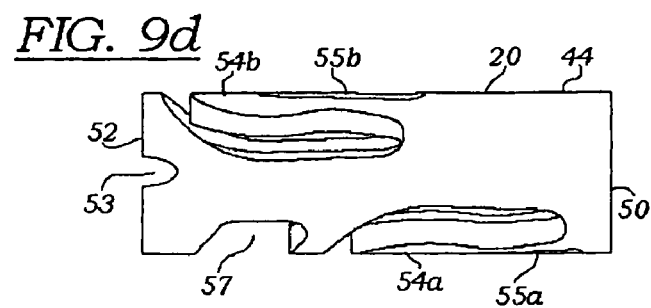
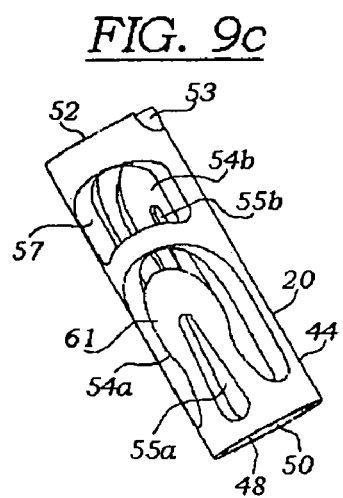
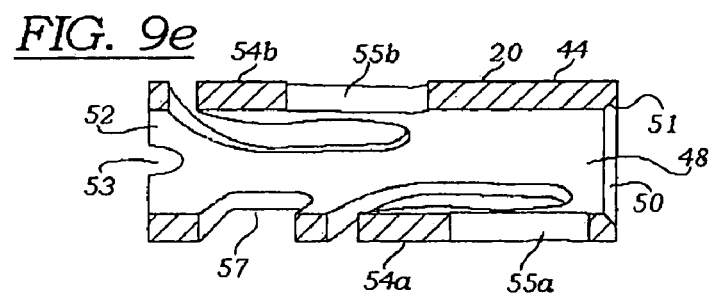
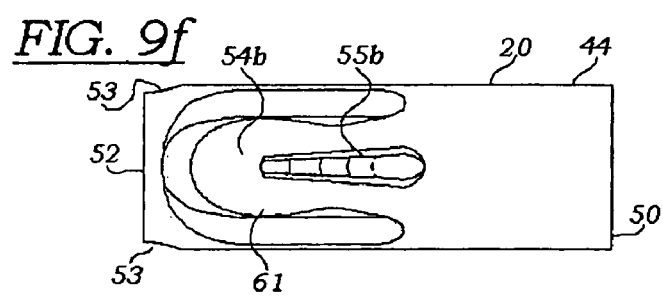

SYSTEM, APPARATUS, AND METHOD FOR FASTENING TISSUE

FIELD OF THE INVENTION

The present invention relates to medical devices and methods. In particular, the present invention relates to a system, apparatus, and method for fastening tissue, and particularly for fastening tissue using a suture and clip.

BACKGROUND OF THE INVENTION

Many medical procedures involve joining tissue pieces. Suturing adjacent tissue pieces is commonly performed using suture, particularly where the tissue pieces are easily accessible to the surgeon. In conventional surgical techniques, the surgeon will secure the tissue pieces by forcing a needle and suture material through various portions of the tissue, and then tying a knot in the suture material to secure the tissue pieces.

Minimally invasive surgical techniques have emerged as an alternative to conventional surgical techniques to perform a plurality of surgical procedures. Minimally invasive procedures differ from conventional surgical procedures in that a plurality of devices may be introduced into the body through a small incision. As a result, trauma to the body is greatly reduced, thereby decreasing the recovery time of the patient.

Percutaneous and other minimally-invasive methods of surgery, where the surgery may be performed remotely via catheters, often include the need to fasten tissue pieces which the surgeon cannot directly access. For example, in percutaneous operations to close a patent foramen ovale (PFO), adjacent tissue pieces on either side of the PFO must be secured together via a catheter. In so-called edge-to-edge valve repairs, adjacent valve leaflet edges are secured together to restore valve functionality. Further information on these and similar procedures for which the current invention can be applicable are disclosed in the following references, the entire contents of which are expressly incorporated herein by reference: U.S. Pat. No. 6,626,930 issued to Allen et al.; U.S. patent application Ser. No. 10/106,583, filed Mar. 26, 2002 and entitled, "Sequential Heart Valve Leaflet Repair Device and Method of Use"; U.S. patent application Ser. No. 10/233,879, filed Sep. 3, 2002 and entitled "Single Catheter Mitral Valve Repair Device and Method"; U.S. patent application Ser. No. 10/389,721, filed Mar. 14, 2003 and entitled "Mitral Valve Repair System and Method of Use"; and patent application Ser. No. 11/174,143, filed Jun. 30, 2005 and entitled "System, Apparatus, and Method for Repairing Septal Defects."

One challenge presented when performing a heretofore conventional surgical procedure using a minimally invasive technique is to remotely position and secure sutures to an area of interest. In minimally invasive surgical techniques the surgeon's access to the approximation site is greatly reduced. One method involves using a surgical device to attach the suture material to the tissue, while allowing for sufficient suture so that the suture ends lead outside of the patient's body for easy access by the surgeon. The surgeon can remotely form a loose knot in the suture material and advance the knot to the tissue within the patient using a so-called "knot pusher." The surgeon can then remotely tighten the suture and knot, thereby securing the tissue pieces together.

Several knot pushing devices are known which permit an operator to push suture knots which have been formed extracorporeally towards tissue to be sutured. For example, U.S. Pat. No. 5,769,863, issued to Garrison et al., discloses a surgical knot pusher having an elongated body connected to a pushing head. The pushing head engages a portion of suture material containing a knot and is advanced to the area of interest, thereby "throwing" the knot. Once the suture knot is placed the knot pushing device is removed and a cutting implement is introduced into the body and cuts the remaining suture material. The remaining suture material is then removed. Another example of a knot pusher is disclosed in U.S. Pat. No. 6,860,890, entitled "Surgical Knot Pushing Device and Method of Use," the entire contents of which are expressly incorporated herein by reference.

Another method of securing suture material involves using a clip to secure the suture together. The clip can be delivered remotely by advancing the clip along a relatively long suture line to the area of interest, and then deploying the clip such that the clip secures the suture in place. With the clip thus secured, the excess suture can be cut and removed from the patient. An example of such a clip as well as methods and devices for use therewith are disclosed in patent application Ser. No. 11/174,357 filed Jun. 30, 2005 and entitled "System, Apparatus, and Method for Fastening Tissue," the entire contents of which are expressly incorporated herein by reference.

In light of the foregoing, there is presently a need for improved systems for remotely securing tissue pieces. More specifically, there is a present need for an improved method, apparatus, and system for fastening tissue. The current invention meets this need.

BRIEF SUMMARY OF THE INVENTION

The present invention solves the problem of effectively securing tissue pieces using a suture and clip.

The present invention utilizes a clip having a generally tubular shape, with an inner lumen passing through the tube. The inner lumen is sized and configured so that one or more lines of suture may pass therethrough. One or more obstructions extend into the inner lumen. The obstructions may be permanently positioned within the lumen, or may be movable so that they can extend into the lumen to a greater or lesser extent.

The clip may be formed from suitable biocompatible material, including, for example, Nickel-Titanium or other shape-memory alloys, stainless steel, titanium, other metals, various plastics, and other biologically-compatible materials.

In a first embodiment, the clip is formed from a shape-memory material such as nickel-titanium. The obstructions are movable so that the extent of their blocking the inner lumen varies to a lesser and greater extent. With the clip shape-memory material in its austenite state, the obstructions extend into the inner lumen to their greatest extent, so that the clip is in a "locked" configuration wherein the obstructions block movement of any suture line or lines passing through the inner lumen. The austenite state can be set to occur when the clip is generally unstressed and at human body temperature, so that the clip when deployed in the patient's body will be remain biased toward its locked configuration.

The obstructions may be integrally formed with or from the generally tubular body. For example, the obstructions may be tabs cut from the tubular body and then bent or otherwise rotated into the inner lumen to block the inner lumen. The obstructing tabs may be formed from generally horseshoe-shaped cuts in the wall of the tubular body. The tabs can be sized, shaped, positioned, and/or otherwise configured to extend into the inner lumen to varying amounts, depending on the particular application. For example, a tubular structure with relatively thin suture lines passing therethrough may require larger tabs that can extend to a greater extent into the body lumen. Such tabs may be sized so that, when bent into the inner lumen, they extend across 50% or more of the diameter of the inner lumen.

The tubular body can include one or more tabs. Where multiple tabs are present, they may be positioned at various locations along and around the tubular body. For example, they may be positioned at various distances along the length of the body, and/or may be positioned in various configurations around (e.g., on the same side or on opposing sides) the circumference of the tubular body.

The clip can be formed in various ways. In one embodiment, an elongated tube is provided. The elongated tube is cut to a desired length to form the generally tubular body of the clip. The tabs are cut into the generally tubular body (if the tab cutting occurs after the elongated tube has been cut into individual tubular body lengths), or into the elongated tube (if the tab cutting is performed prior to the elongated tube being cut into individual generally tubular body lengths). The cutting of the tube and/or tabs to form the clip can be performed via laser cutting and/or other methods. After the tabs are cut, they are then bent or otherwise manipulated inward so that they obstruct the inner lumen. The clip may be formed from shape memory and/or pseudoelastic materials, such as nickel-titanium. The clip may be formed such that the tabs are biased to extend into and/or otherwise obstruct at least part of the clip inner lumen when the clip material is in the austenite condition. The clip may also be formed such that the tabs, when subject to sufficient stress such as a bending moment, are stressed into a martensite condition wherein they are held out of the way of the clip inner lumen, but will return to their austenite condition where they block the clip inner lumen once the stress is removed.

The clip may be deployed using various devices and/or procedures, such as a fastener catheter which may or may not have an integral suture-cutting apparatus. The fastener catheter may be configured to selectively apply stress to the clip, such as the application of force to move the clip engagement tabs out of the clip inner lumen and into general alignment with the clip outer wall.

In a method according to the invention, the user deploys suture through tissue within a patient's body, leaving one or more suture leads that pass out of the patient's body. A catheter and clip assembly according to the invention is advanced into the patient's body along the suture leads, the clip is positioned at a desired position on the suture adjacent the tissue, the catheter deploys and/or releases the clip at the desired position, and the catheter then cuts the suture leads at a position near the tissue. Alternatively, the suture cutting may be performed by a different catheter or other suture cutting device.

Other objects, features, and advantages of the present invention will become apparent from a consideration of the following detailed description.

BRIEF DESCRIPTION OF THE DRAWINGS

FIG. 1 depicts a side view of a catheter and fastener assembly according to an embodiment of the invention;

FIGS. 2a and 2b show a perspective view of components of a catheter distal portion of an embodiment of the present invention;

FIG. 2c shows a perspective view of the catheter distal portion of the embodiment from FIGS. 2a and 2b assembled and having a fastener attached thereto;

FIG. 4 depicts a side view of a fastener in a closed configuration according to an embodiment of the invention;

FIG. 5 depicts a side view of a fastener in a closed configuration with suture, according to an embodiment of the invention;

FIGS. 9c-9f depict perspective, side, side (in cross-section), and top views, respectively, of a fastener according to an embodiment of the invention;

DETAILED DESCRIPTION OF THE INVENTION

Figure 3C:
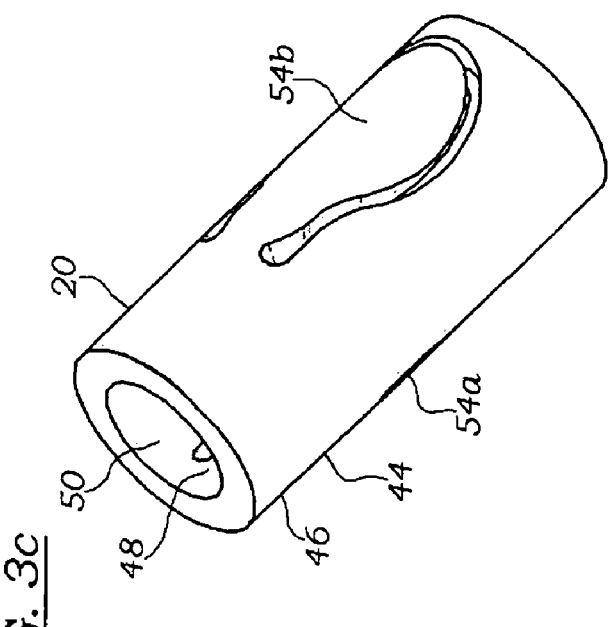
FIGS. 3a, 3b, 3c, and 3d depict side, top, perspective, and distal end views, respectively, of a fastener in an open configuration according to an embodiment of the invention.
Figure 3D:
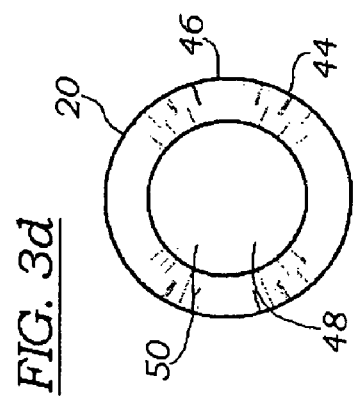

The invention is an apparatus, system, and method for securing suture. More specifically, the invention provides for percutaneous or other minimally-invasive techniques of securing suture.

FIG. 1 depicts an embodiment of a fastener catheter 10 according to an embodiment of the invention. The fastener catheter 10 has a generally tubular main catheter body 12, a proximal end 14, and a distal end 16. The proximal end 14 includes a handle knob 18. The distal end 16 includes a suture fastener clip 20 positioned thereon. The fastener catheter 10 may be manufactured in a variety of shapes, sizes, lengths, widths, and biologically-compatible materials as desired for a particular application.

The generally tubular catheter main body 12 has a longitudinal inner lumen 22 therethrough which terminates in a distal opening 24 having a surrounding edge 25. A longitudinally slidable inner body 26 is slidably positioned within the main body 12. The inner body 26 includes an inner tubular member distal end 28 which extends out of the main body distal opening 24. The inner tubular member distal end 28 itself includes an inner tubular member distal opening 30, which leads to an inner body lumen 32. These and other features are depicted in additional detail in FIGS. 2a-2c, which illustrate (in exploded fashion in FIGS. 2a-2b, and assembled in FIG. 2c), distal portions of the fastener catheter 10.

The inner body 26 includes a suture recess 34 formed in the side thereof, which in turn is in communication with the inner body lumen 32. Inner body 26 also includes a pin 36 extending radially outward therefrom. The main catheter body 12 has a cutting recess 38 formed in an axial side thereof and a cutting member 40 which, in the embodiment depicted, is on a proximal edge of cutting recess 38. A pin recess in the form of slot 42 extends parallel to the axis of the main body 12 and radially through to main body lumen 22. The slot 42 is thus configured to receive pin 36 in sliding relation.

In FIG. 2c, the inner body 26 is slidably positioned within main catheter body 12, such that suture recess 34 is in alignment with cutting recess 38. Pin 36 is in slidable communication with slot 42 thereby permitting relative linear motion, but preventing relative rotational motion, between inner body 26 and main body 12. A fastener clip 20 is positioned on the inner body distal end 28, which protrudes from the main body distal opening 24. The fastener clip, which is depicted in greater detail in FIGS. 3a-5b, includes a generally tubular body 44 having an outer wall 46, an inner lumen 48, a clip distal opening 50, a clip proximal opening 52, and engagement tab 54. As depicted in FIG. 2c, the fastener clip 20 has been placed on inner member distal end 28 by deflecting the engagement tab 54 radially outward until it is generally flush with the clip outer wall 46. Accordingly, the fastener clip 20 is secured to the inner body distal end 28 by means of the frictional engagement between the engagement tab 54 and the outer surface of inner body 26. Suture 56 extends from the fastener clip 20, with suture leads 56a and 56b extending through the clip inner lumen 48 via the clip distal opening 50, engagement tab 54, and proximal opening 52, passing through catheter inner member distal opening 30 and inner member lumen 32, exiting the inner member 26 via suture recess 34, and exiting the side of main body 12 through cutting recess 38.

FIGS. 3a through 3d illustrate a fastener clip 20 of the present invention in an "open" configuration, while FIG. 4 depicts the fastener clip 20 in a "closed" or "locked" configuration. The fastener clip 20 may be manufactured from a variety of materials including, for example, nickel-titanium alloys, shape-memory alloys, stainless steel, titanium, various plastics, and other biologically-compatible materials. Fastener clip 20 has a generally tubular body 44 and an outer wall 46, and includes a distal opening 50 leading to an internal attachment lumen 48 extending axially through the fastener clip 20 to a proximal opening 52. The fastener clip 20 includes one or more engagement tab(s) 54a, 54b formed in the fastener clip 20 and configured to leave the inner lumen relatively unobstructed when in the "open" configuration as depicted in FIGS. 3a-3d, and to at least partially obstruct the inner lumen 48 when in a "closed" configuration, as depicted in FIG. 4.

Figure 3A:
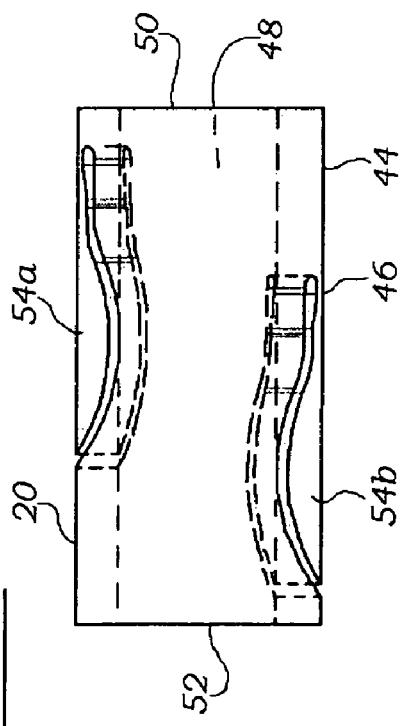
Figure 3B:
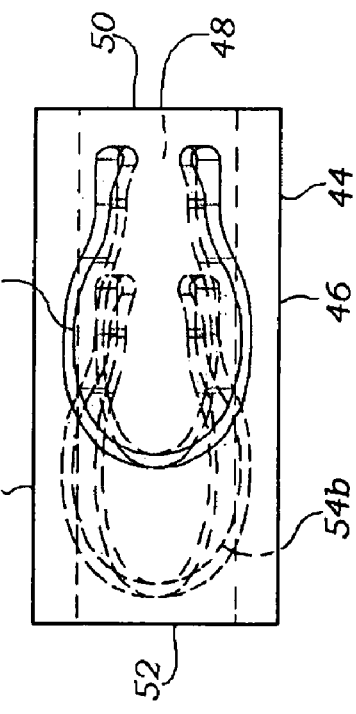

The distal opening 50, proximal opening 52, inner lumen 48, and engagement tabs 54a, 54b are sized and configured (when the engagement tabs 54a, 54b are in the "open" configuration of FIGS. 3a-3b) to slidingly receive a first suture lead 56a and a second suture lead 56b therein, as was depicted in FIG. 3a. Prior to deployment, engagement tabs 54a, 54b are moved to their "open" configuration by being deflected radially out of the inner lumen 48 such that the engagement tabs 54a, 54b are essentially flush with the fastener outer wall 46, thereby leaving the inner lumen 48 essentially unobstructed, or at least unobstructed to the extent necessary for the suture lines 56a, 56b to slidingly pass within the lumen 48. As was depicted in FIG. 3a, the inner lumen 48 (with engagement tabs 54a, 54b in their open configuration) provides a relative large and relatively unobstructed passage sufficient to permit suture leads to slide therethrough.

Upon deployment, i.e. after the suture leads 56a and 56b have been retracted and/or tightened to their desired position and the fastener clip 20 advanced to it's desired deployment position, engagement tabs 54a, 54b are deflected or permitted to spring back toward the central axis of the fastener clip 20 such that the inner lumen 48 is at least partially blocked, whereupon the engagement tabs 54a, 54b engage against and secure the suture leads 56a, 56b, as depicted in FIG. 5. The "closed" engagement tabs 54a, 54b cause the suture leads 56a, 56b passing therethrough to adopt a "serpentine" path through the clip inner lumen 48. This serpentine path, combined with the friction on the suture from the engagement tabs 54a, 54b, serves to lock the suture 56a, 56b in place and prevent longitudinal movement thereof within the clip lumen 48. The suture 56a, 56b is thus held by the combination of tab 54a, 54b to inner wall interaction/forces and by the tortuous path that the tabs 54a, 54b force the suture to follow, which provides more surface area contact with the suture 56a, 56b to increase retention. In the embodiment of FIG. 5, the suture lines 56a, 56b are depicted as being relatively thin as compared to the clip lumen 48. However, depending on the particular application, suture that is of a much greater thickness would be used with a clip according to the invention. If used with thicker suture(s), a clip 20, and particularly the tabs 54a, 54b, such as that depicted in FIG. 5 would assume a somewhat different shape once deployed. With a thicker suture line or lines, the tabs 54a, 54b would each be forced back outward (i.e., toward their "open" configuration") by the suture.

Depending on the particular embodiment, including the materials from which a particular fastener is made, the engagement tab(s) 54 may be biased to spring toward a desired position, which may be either the closed configuration or the open configuration, depending on the particular application.

Figure 6A:
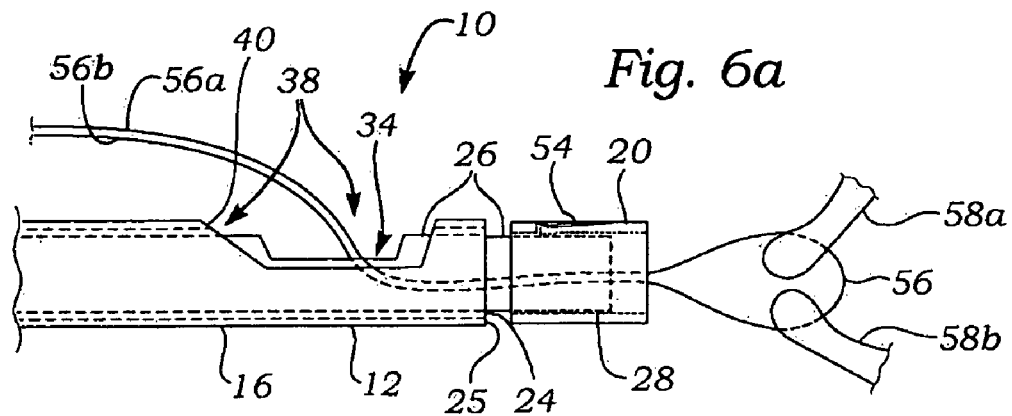
FIGS. 6a-6c depict side views of a catheter distal portion with a fastener and suture according to an embodiment of the invention.
Figure 6B:
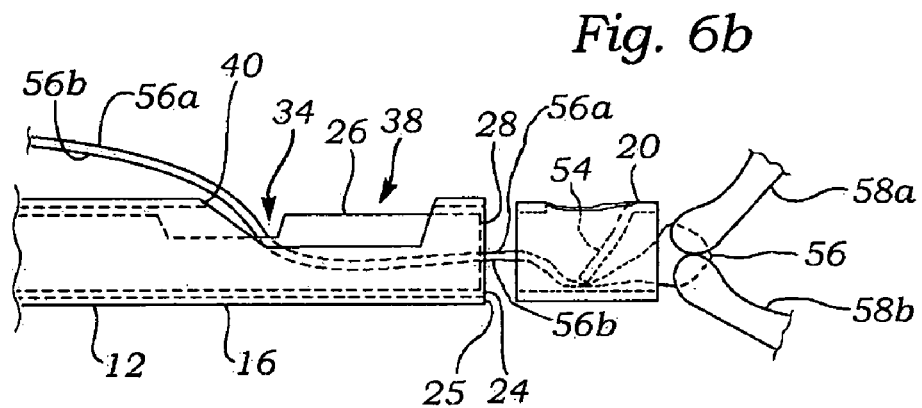
Figure 6C:
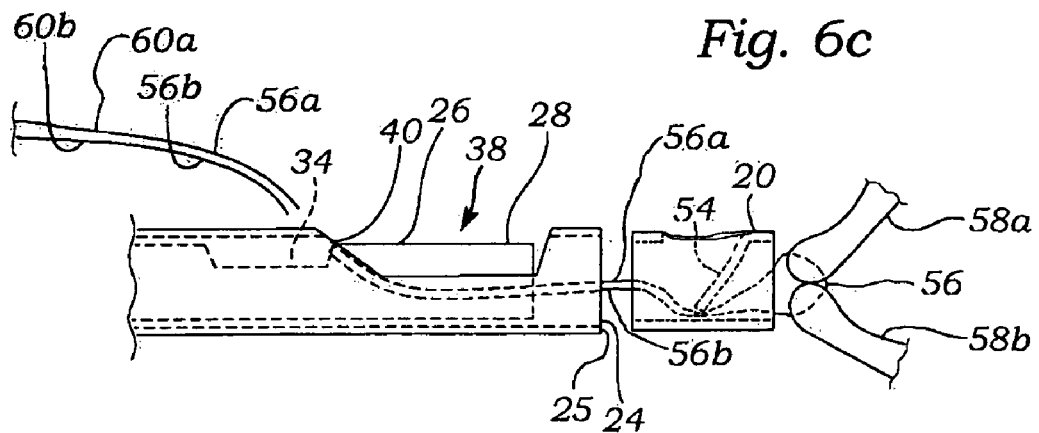

FIGS. 6a-6c depict the distal end 16 of a catheter 10 according to an embodiment of the invention in various configurations. FIG. 6a depicts the catheter inner body distal end 28 extending from catheter main body distal opening 24, with a fastener clip 20 positioned on the inner body distal end 28. A suture line 56 extends through tissue portions 58a, 58b into the assembly with suture leads 56a, 56b exiting the inner member 26 via suture recess 34, and exiting the side of main body 12 through cutting recess 38.

In FIG. 6b, the catheter inner body distal end 28 has been retracted into the main body distal opening 24. With the inner body distal end 28 retracted, the fastener clip 20 has been released from the catheter 10. As the inner body distal end 28 was retracted, the fastener clip 20 engaged against the distal edge 25 of the main body distal opening 24 and was forced off of the inner body distal end 28 at a position adjacent the tissue portions 58a, 58b. With the fastener clip 20 freed from the catheter, the clip engagement tab 54 has retracted axially, thereby partially or completely closing the clip proximal opening 46 and engaging the suture leads 56a, 56b. With the fastener clip 20 in this closed configuration, the leads 56a, 56b are held fast and cannot move longitudinally within the fastener clip 20. Note that the leads 56a, 56b still pass into the catheter 10, exiting the inner body 26 via suture recess 34 and exiting the side of main body 12 through cutting recess 38.

FIG. 6c depicts the inner body 26 retracted even further within main body 12. As the inner body 26 was retracted, the suture leads 56a, 56b were caught in the engagement between the cutting member 40 of the main body 12 and a suture recess distal edge 35 of the inner body 26. The engagement of the cutting member 40 with the suture recess distal edge 35 cuts the suture leads 56a, 56c, allowing the user to remove the excess portions 60a, 60b thereof.

Although the embodiment depicted in FIGS. 6a-6c includes a cutting member 40 on the main body, a cutting member could be placed elsewhere, either in addition to or in lieu of the main body cutting member. For example, a cutting member could be placed on the suture recess distal edge 35 of the inner body 26. Or both the suture recess distal edge 35 and the main body cutting member may be unsharpened edges, with the suture being cut by the sheering force created by the cooperation between the relatively unsharp edges.

Figure 7:
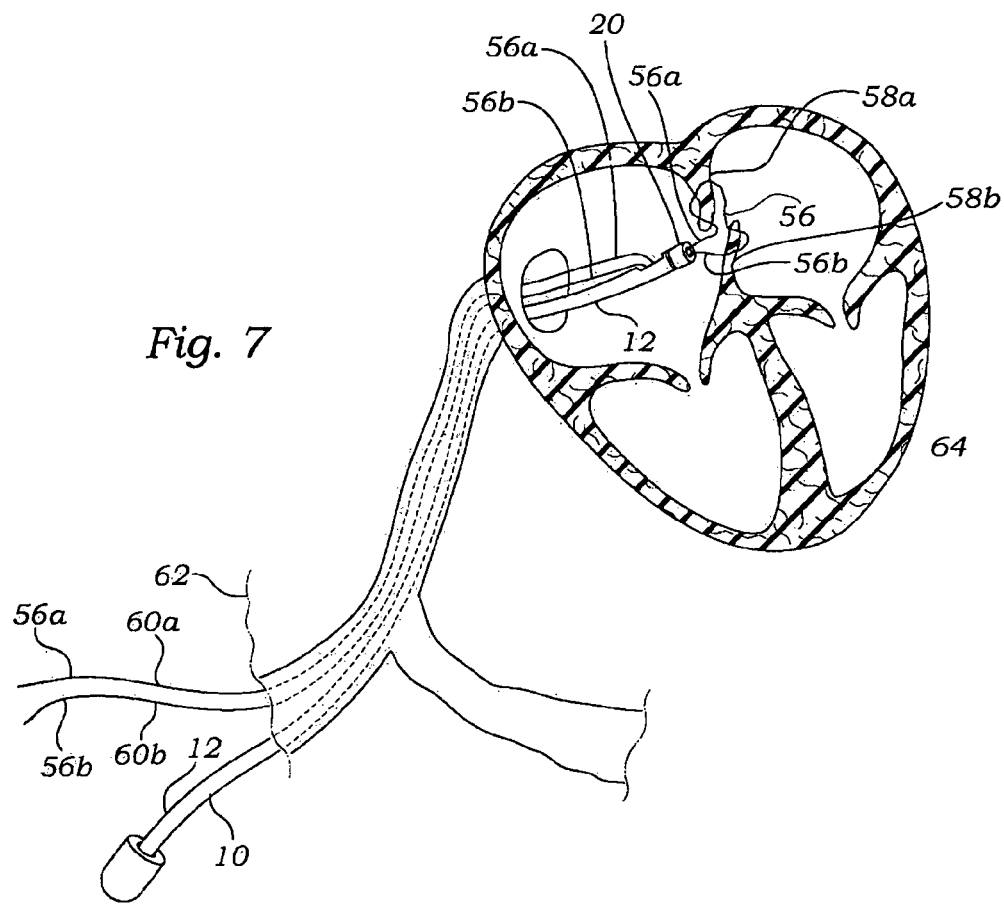
FIG. 7 illustrates a catheter advanced within a patient's vasculature and adjacent tissue pieces to be joined according to an embodiment of the invention.

FIG. 7 depicts the fastener catheter 10 deploying a fastener clip 20 at a desired location in a patient's body 62. In the embodiment depicted, the suture 56 has previously been passed through the desired tissue structures 58a, 58b within the patient's body 62, which in the embodiment depicted is tissue with the patient's heart 64, and specifically tissue adjacent an atrial septal defect, such as a patent foramen ovale (PFO). With the suture 56 passing through the tissue 58a, 58b and the suture leads 56a, 56b passing out of the patients' body 62, the user can advance the fastener catheter 10 into the vicinity of the tissue 58a, 58b, as shown in FIG. 7. The fastener catheter will advance along the suture leads 56a, 56b and, if present, along a guidewire (not shown). Note that in the particular embodiment depicted, the suture 56 has been passed twice through each portion of tissue 58a, 58b, which will tend to hold the adjacent wall-like tissue structures 58a, 58b in side-to-side relation, with the clip 20 positioned therebetween, once the suture 56 is tightened and secured with the clip 20.

Various methods and/or systems can be used to pass the suture through the desired tissue. Moreover, although FIG. 7 depicts the invention used to repair a PFO, the invention can also be used in other procedures, including tissue treatments such as so-called "edge-to-edge" mitral valve repairs involving edge-to-edge suturing of adjacent mitral valve leaflets. In another procedure, embodiments of the system may be used to occlude a left atrial appendage for decreasing the risk of arterial embolism. In one preferred procedure, tissue along the ostium of the left atrial appendage is sutured together to prevent blood from flowing in and out. This procedure is preferably performed using a transseptal approach and may be performed after delivering an expandable device into the left atrial appendage for filling the volume and further preventing the formation of thrombus. In another method of use, the system may be used for occluding fallopian tubes in a minimally-invasive sterilization technique. In this procedure, the system is advanced into a fallopian tube and suture is applied to pull opposing walls together, thereby blocking the tube. In still other applications, the system may be used to treat organ prolapse, such as uterine or bladder prolapse. This procedure may be used to pull tissue together in a percutaneous procedure to treat proplapse by providing additional support at locations wherein muscles and/or ligaments have become stretched or have been otherwise damaged.

Additional information on procedures for which the current invention can be applicable are disclosed in the following references, the entire contents of which are expressly incorporated herein by reference: U.S. Pat. No. 6,626,930 issued to Allen et al.; U.S. patent application Ser. No. 10/106,583, filed Mar. 26, 2002 and entitled, "Sequential Heart Valve Leaflet Repair Device and Method of Use"; U.S. patent application Ser. No. 10/233,879, filed Sep. 3, 2002 and entitled "Single Catheter Mitral Valve Repair Device and Method"; U.S. patent application Ser. No. 10/389,721, filed Mar. 14, 2003 and entitled "Mitral Valve Repair System and Method of Use"; and patent application Ser. No. 11/174,143, filed Jun. 30, 2005 and entitled "System, Apparatus, and Method for Repairing Septal Defects."

The user can initially tighten the suture 56 to determining whether the suture 56 is properly positioned in accordance with the desires of the user in the particular application. The advancement of the fastener catheter 10, combined with the user holding (and possibly pulling on) the suture leads 56a, 56b, causes the suture 56 to tighten. The user can verify the effectiveness of the tightened suture by monitoring various patient functions. For example, the user may confirm the result by monitoring blood flow using radiopaque dyes combined with fluoroscopy. If the user is dissatisfied with the results when the suture is initially tightened, the user can remove the suture entirely from the patient's body and repeat the suture deployment to try to achieve a better positioning of suture. If, however, the user is satisfied with the results, the user can release the fastener clip 20 from the catheter 10. Once the fastener clip 20 is released, the clip securely holds the suture leads 56a, 56b. The user can then cut the suture leads 56a, 56b and remove the excess suture 60a, 60b by simply pulling the excess suture 60a, 60b out of the patient's body 62. The user then withdraws the fastener catheter 10 from the patient, leaving the suture 56 and suture fastener clip 20 in place in the desired tissue. The guidewire, if present, is also removed.

Figure 8A:
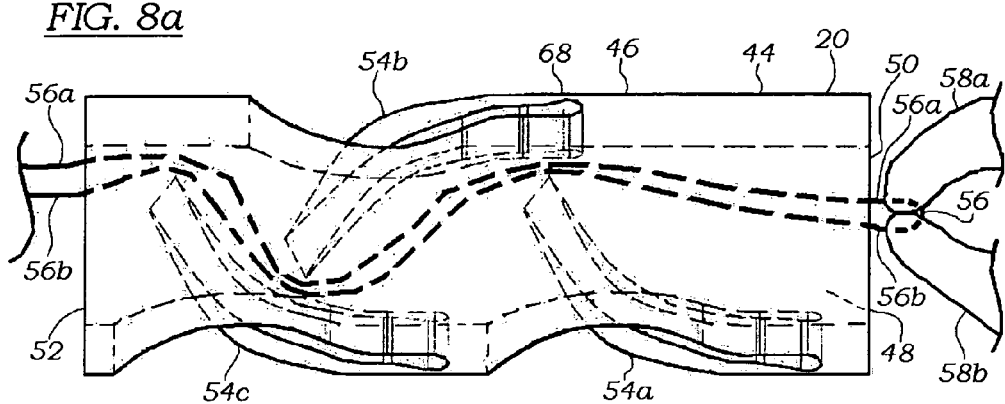
FIGS. 8a and 8b depict a side and top view, respectively, of a fastener according to an embodiment of the invention.
Figure 8B:
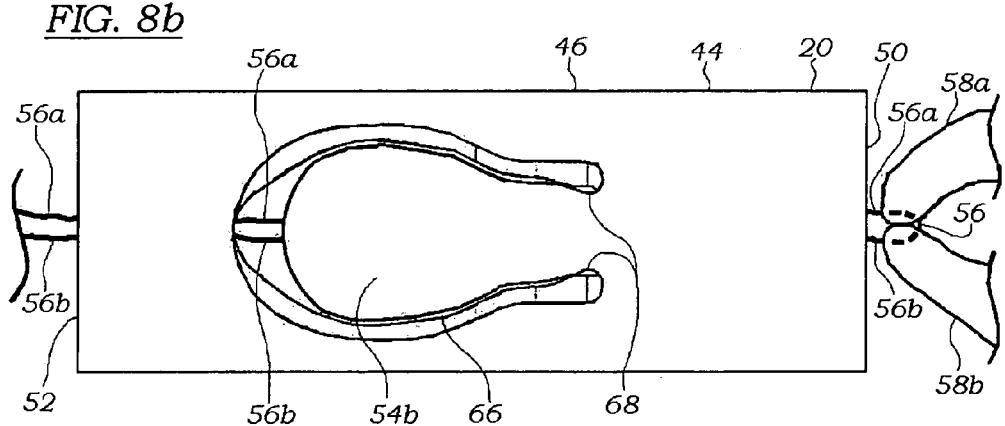

FIGS. 8a and 8b depict a fastener clip 20 according to a further embodiment of the invention. The fastener clip 20 includes three (3) engagement tabs 54a-c, with the engagement tabs 54a-c positioned on alternating sides of the fastener clip 20. FIGS. 8a and 8b depict the clip in the closed configuration, wherein the engagement tabs 54a-c extend into the clip inner lumen 48 from opposing sides, causing the suture line 56 passing therethrough to adopt a relatively complicated "serpentine" path through the clip inner lumen 48. This serpentine path, combined with the friction on the suture from the engagement tabs 54a-c, serves to lock the suture 56 in place and prevent longitudinal movement thereof within the clip lumen 48. The suture 56 is thus held by the combination of tab to inner wall interaction/forces and by the tortuous path that the tabs force the suture to follow, which provides more surface area contact with the suture to increase retention.

Note that the number, shape, and configuration of the engagement tabs along the clip can vary, depending on the particular application. For example, the engagement tabs can be positioned on opposing sides of the clip (as in FIGS. 3a-3d and 8a-8b), on the same side of the clip, in a spiral pattern about the clip body, etc.

In the embodiment of FIGS. 8a and 8b, the engagement tabs 54a-54c are all formed from generally horseshoe-shaped cut-outs 66, and the "open" end 68 of each cut-out 66 faces in the same direction, namely toward the clip distal opening 50 and the tissue pieces 58a, 58b being fastened by the suture 56. This type of configuration (i.e., with the tabs all facing in the same direction) may, depending on the suture and cut-out size, etc., permit the fastener clip 20 to be advanced distally along the suture line(s) even when the fastener clip 20 and tabs 54a-54c are in their "closed" configuration. Such post-deployment clip advancement may be desirable where there is unwanted slack in the suture lines 56a, 56b after the fastener clip 20 has been released and has assumed its "closed" configuration. As the fastener clip 20 is advanced distally (e.g., by pushing) toward the tissue 58a, 58b, the suture lines 56a, 56b pass proximally through the clip inner lumen 48 and engage against the ends of the tabs 54a-54c, thereby pushing the tabs 54a-54c in hinge-like fashion toward their "open" configuration, thereby at least partially opening the clip inner lumen 48 so that the suture lines 56a, 56b can pass proximally through the fastener clip 20. If the fastener clip 20 is moved proximally along the suture lines 56a, 56b, however, the suture lines 56a, 56b will tend to force the tabs 54a-54c into their most "closed" position, thereby preventing movement of the suture lines 56a, 56b through the clip 10.

Figure 9A:
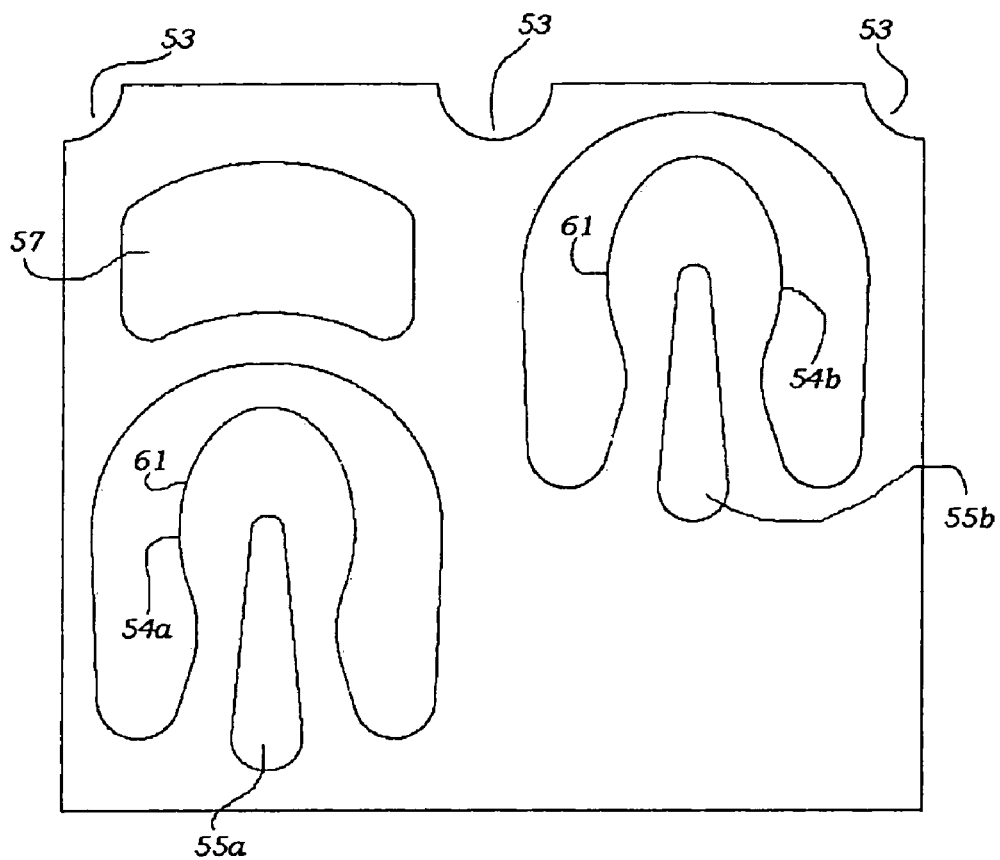
FIGS. 9a-b depict front and detail views of a clip pattern according to an embodiment of the invention.
Figure 9B:
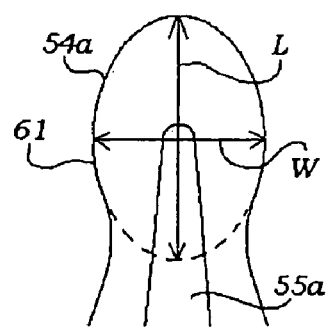
Figure 9G:
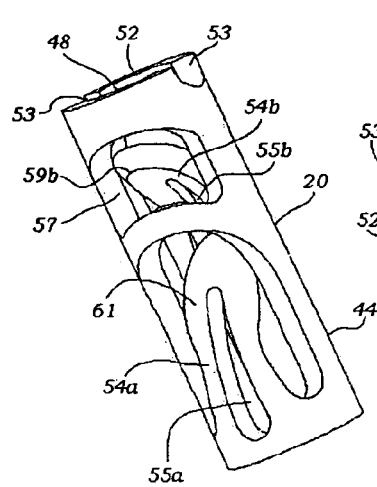
FIGS. 9g-9j depict perspective, side (in cross-section), top, and end views, respectively, of a fastener according to an embodiment of the invention.

FIGS. 9a-9j depict a further embodiment of the invention. The fastener clip 20 is initially formed from a generally tubular body 44, such as a portion of nitinol hypotube into which the desired pattern of tabs 54a, 54b, windows 55a, 55b, 57, and other openings 53, etc. is formed. FIGS. 9a and 9b depict in "flat" form (i.e., projected onto a flat instead of cylindrical surface) the particular pattern created in the hypotube to form the clip 20 of FIGS. 9c-9j. Note that the pattern of tabs 54a, 54b, windows 55a, 55b, 57, and other openings 53, etc., can be formed in various ways, depending on the particular application. In one embodiment, the pattern is formed by laser cutting the desired pattern into a portion of a hypotube or other generally tubular body. FIGS. 9c-9f depict the generally tubular body 44 after the desired pattern has been cut into the generally tubular body, but before the tabs 54a, 54b have been bent or otherwise moved and set into position to block the inner lumen 48. The configuration depicted in FIGS. 9c-9f also corresponds with the "open" configuration of the clip 20, wherein the tabs 54a, 54b are held by the catheter in generally alignment with the outer wall 46 of the generally tubular body 48. FIGS. 9g-9j depict the clip 20 after the tabs 54a, 54b have been bent into and set in their "closed" position, wherein they at least partially block the inner lumen 48.

The clip 20 includes a beveled inner edge 51 at the clip distal opening 50. The beveled inner edge 51, which in the embodiment depicted is at an angle of about 45 degrees, can assist in threading suture into the clip 20 through the clip distal opening 50. The clip 20 also includes two generally semi-circular notch-like openings 53 at the clip proximal opening 52. The notch-like openings 53 can aid in processing of the clip during manufacture, e.g., permitting easy alignment and holding of the clip 20 during bending and/or shape setting of the tabs 54a, 54b, etc. After clip manufacturing is complete, the notch-like openings 53 can interact with corresponding structure on the catheter distal end to assist in alignment and positioning of the clip 20 on the catheter distal end. The clip 20 includes tabs 54a, 54b having inner window openings 55a, 55b that enhance the flexibility while maintaining strength of the tabs 54a, 54b, and also reduces stress on the hinge-like portion where each tab 54a, 54b connects to the generally tubular body 44 of the clip 20.

Figure 9H:
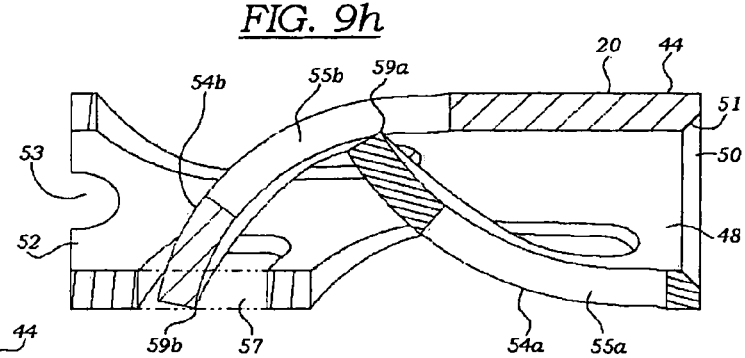
Figure 9I:
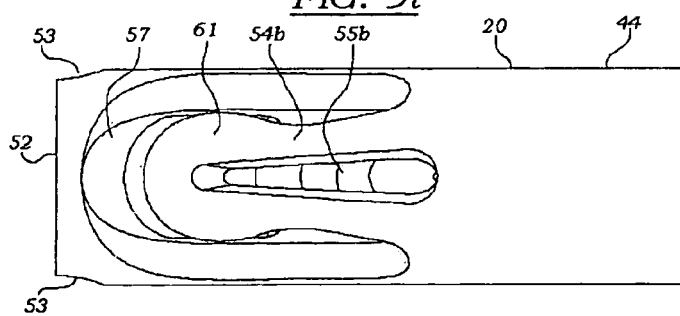

The clip 20 of FIGS. 9g-9j also has a proximal window opening 57 into which the proximal tab 54b is bent, so that the trailing edge 59b of the proximal tab 54b extends into the proximal window opening 57. Note that the trailing edge 59b of the proximal tab 54b remains within the window opening 57, and does not extend beyond the clip outer wall 46, as depicted in FIG. 9h. The proximal window opening 57 permits the proximal tab 54b to be bent to a position just beyond the boundary of the clip inner lumen 48, thereby compensating for tab recovery when the clip 20 is deployed to the closed configuration. Similarly, the trailing edge 59a of the distal tab 54a is bent to the tube inner surface, with the trailing edge 59a of the distal tab 54a resting in the inner window opening 55b of the proximal tab 54b. Note, however, that once the clip 20 is deployed with suture therein, the tabs 54a, 54b may be forced by the suture lines(s) back towards their "open" configuration.

Figure 9J:
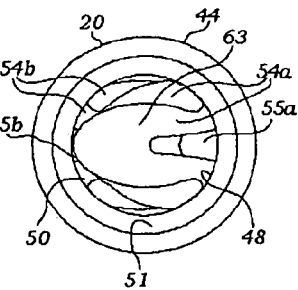

The generally elliptically-shaped portion 61 of each the tabs 54a, 54b, which is depicted in some detail in FIG. 9b (with the dashed portion depicting an imaginary completion of the "ellipse" that forms the actual tab) has a width W (i.e., minor axis) that is approximately equal to (but still slightly less than) the diameter of the clip inner lumen 48. The generally elliptical shaped portion 61 has a length L (i.e., major axis) that is greater than the diameter of the clip inner lumen 48. These dimensions permit each tab 54a, 54b, when in the closed configuration, to fit within the clip inner lumen 48 and still close off essentially the entire diameter of the clip inner lumen 48 (as depicted in end view FIG. 9j), thereby securely holding any suture passing therethrough. Note that because the pattern of tabs and windows was laser-cut in a radial manner into the generally tubular body 44 of the clip 20, the tab 54a has an inner surface having an "inner" elliptically-shaped portion 63 that is somewhat smaller in width than its corresponding "outer" elliptically-shaped portion 61 discussed above. Accordingly, the relatively narrow width of the tab inner elliptically-shaped portion 63 only partially obstructs the inner lumen 48, as shown in FIG. 9j. However, the tab 54a outer surface has the full width W of the elliptically-shaped portion 61 shown in FIG. 9b (which is hidden from the view of FIG. 9j, which is looking down the distal end 52), and it is this width (W) of the "outer" elliptically-shaped portion 61 that obstructs the remaining diameter of the inner lumen 48.

Note that for a tab that is bent at a greater angle (e.g., 90 degrees) into the clip inner lumen 48 than is depicted in FIGS. 9g-9j, the tab could have a more circular shape and still obstruct essentially the entirety of the clip inner lumen. For example, a tab that was to be bent at 90 degrees into the clip inner lumen could have a substantially circular shape, i.e., where the minor axis would be substantially equal to the major axis. Similarly, a tab that is bent at a lesser angle into the clip inner lumen than is depicted in FIGS. 9g-9j would need a more eccentric elliptical shape, where the elliptical portion major axis would be substantially larger than the diameter of the inner lumen, in order to close off substantially all of the inner lumen when in the closed configuration.

The dimensions of the clip can vary depending on the particular application. In one embodiment, a clip 20 such as that depicted in FIGS. 9h-9j has a length of about 0.13 inches, an inner lumen diameter of about 0.030 inches, and an outer diameter of about 0.046 inches. A clip of this size can receive and secure multiple suture lines having various diameters, including sutures having diameters ranging from 0.006 to 0.008 inches. Other clip dimensions are also within the scope of the invention, with the clip dimensions varying depending on aspects of the particular application, e.g., suture type and diameter, the type of tissue to be repaired, the number of suture lines being secured by the clip, etc. Additionally, although the particular embodiment depicted have used the clip to secure two suture lines, a clip according to the invention could be used to secure a single suture line or multiple suture lines. For multiple suture lines, two or more of the multiple suture lines could be portions of a common suture line. For example, a clip could be used to secure four suture lines, with two of those suture lines being opposing portions of a first common suture line and the other two suture lines being opposing portions of a second common suture line.

Figure 10:
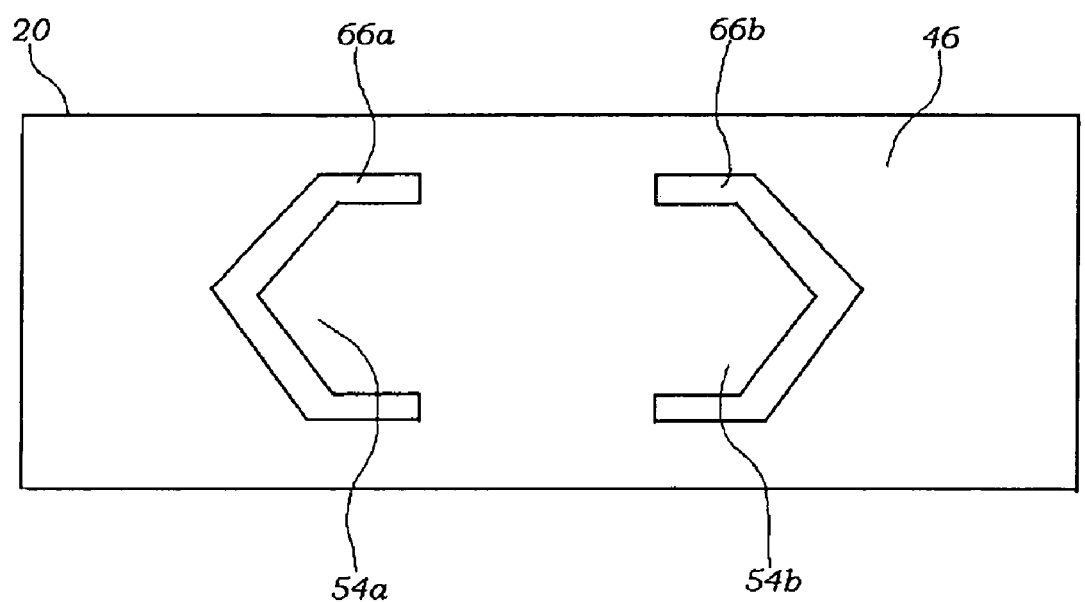
FIG. 10 depicts a top view of a fastener according to an embodiment of the invention.

Note that the embodiments of FIGS. 8a-8c and 9a-9j are only a few examples of many that are within the scope of the invention. Depending on the particular embodiment, the tab cut-outs 66 could be formed in various shapes, and they could be aligned in a common direction with other cutouts, be in opposite directions of alignment, and/or could be positioned in various directions along the clip outer wall 46. For example, in the embodiment of FIG. 10, the cut-outs 66a, 66b are generally wedge- or chevron-shaped, and they are aligned in opposing directions along the clip outer wall 46. The edges of the cut-outs could be shaped with various geometric shapes, e.g., serrated edges, etc. Various other shapes and configurations of cut-outs are within the scope of the invention, depending on the particular application.

Figure 11A:
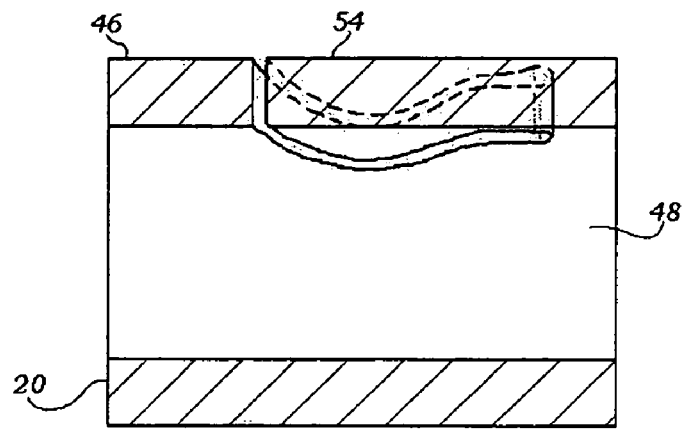
FIGS. 11a-11c depict side views, in cross-section, of fasteners according to various embodiments of the invention.
Figure 11B:
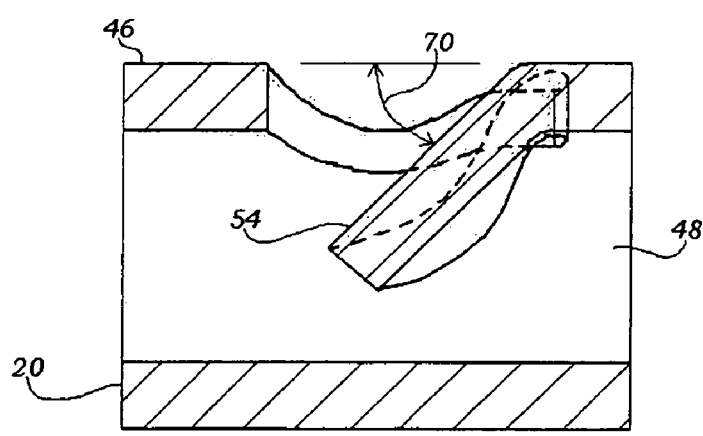
Figure 11C:
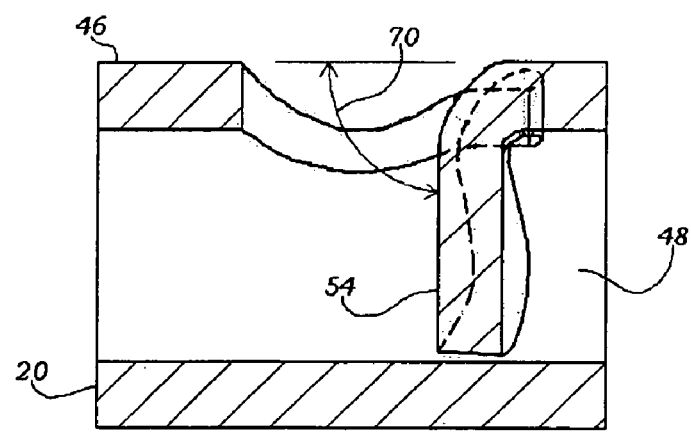

FIGS. 11a-11c depict in cross-section an engagement tab 54 in various configurations. In the embodiment of FIG. 11a, the engagement tab 54 is generally aligned with the clip outer wall 46, so that the clip inner lumen 48 is generally unobstructed. In FIG. 11b the engagement tab 54 is positioned to extend partially into the lumen 48, with the angle 70 between the engagement tab 54 and clip outer wall 46 being on the order of 45 degrees. FIG. 11c depicts the engagement tab 54 extending to a maximum extent into the clip lumen 48, with the angle 70 between the engagement tab 54 and clip outer wall 46 being on the order of 90 degrees. Note that various angles 70 are within the scope of the invention, depending on the particular embodiment and such factors as the size of the suture, the size of the clip, the percentage of the inner lumen that is desired to be obstructed, the length of the engagement tab with respect to the inner diameter of the lumen, etc.

Figure 12A:
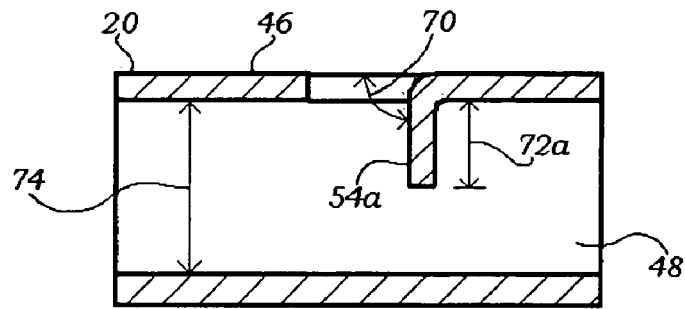
FIGS. 12a-12c depict side views, in cross-section, of fasteners according to various embodiments of the invention.
Figure 12B:
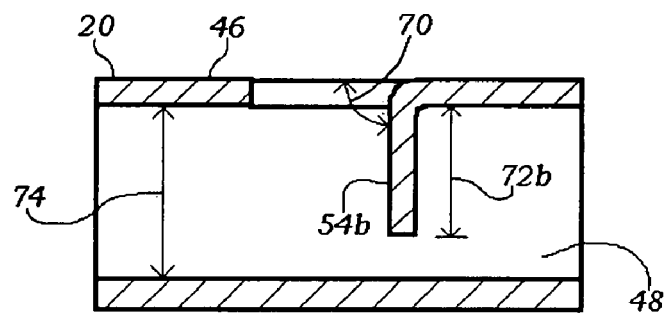
Figure 12C:
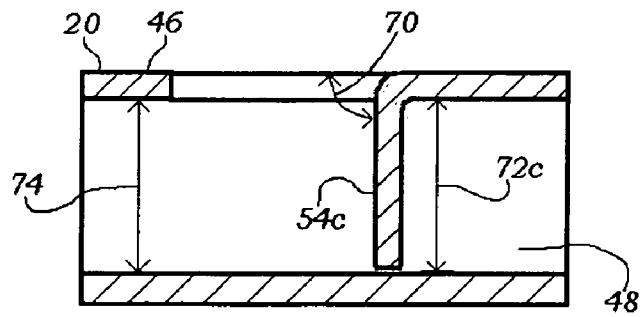

FIGS. 12a-12c depict clips 20 having various lengths 72 of engagement tabs 54. Although the embodiments of FIGS. 12a-12c are all depicted as having an angle 70 of about 90 degrees, it is noted that other angles are within the scope of the invention, as discussed above with respect to FIGS. 11a-11c. In FIG. 12a, the engagement tab 54a has a length 72a equal to about 50% of the clip inner lumen diameter 74. In FIG. 12b, the engagement tab 54b has a length 72b of about 75% of the clip inner lumen diameter 74, while in FIG. 12c the engagement tab 54c has a length 72c of about 100% of the clip inner lumen diameter 74. Note that, as with the angle 70, the engagement tab length 72 for a particular clip can vary depending on the particular application and still fall within the scope of the invention.

Figure 13A:
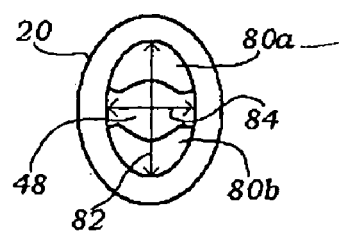
FIGS. 13a and 13c depict end views of a fastener according to a further embodiment of the invention.
Figure 13B:
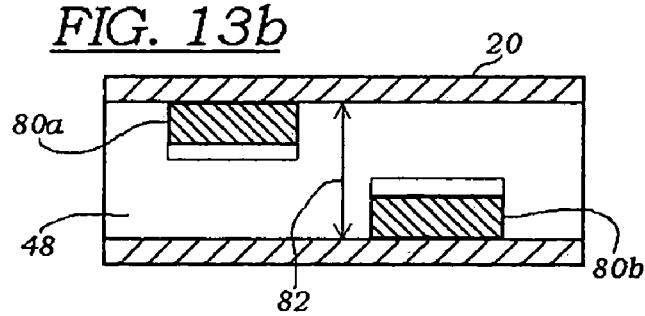
FIGS. 13b and 13d depict side views, in cross-section, of the fastener of FIGS. 13a and 13c.
Figure 13C:
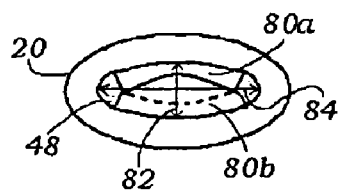
Figure 13D:
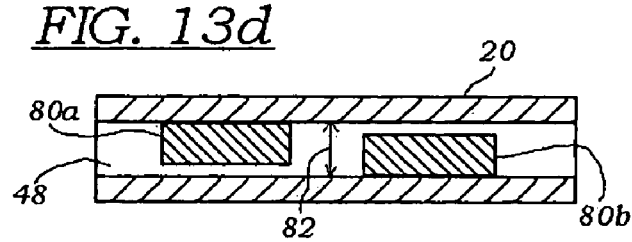

While engagement tabs 54 have been discussed with particularity, other structures may be used to block a clip inner lumen. For example, inward-facing obstructions such as bumps and/or ridges could be positioned on the inner surface of the clip inner lumen so that the bumps and/or ridges at least partially block the inner lumen. One such embodiment is depicted in FIGS. 13a-13d, wherein a clip 20 includes inner bumps 80a, 80b extend into the clip inner lumen 48. In FIGS. 13a and 13b, the clip 20 is in the open configuration, with the clip 20 being generally oval-shaped when viewed from the end (as seen in FIG. 13b), with a height 82 that is greater than the width 82. This open configuration places the bumps 80a, 80b at opposite ends of the largest dimension (i.e., the height 82) of the inner lumen 48, so that the inner lumen 48 has a size sufficient for suture to slidingly pass therethrough. FIGS. 13c and 13d depict the same clip 20 in its closed configuration, wherein the clip 20 has assumed a generally "flattened" configuration when viewed from the end (as seen in FIG. 13d) so that the width 84 is now greater than the height 82. With the bumps 80a, 80b now at opposite ends of the shorter dimension (i.e., the height 82) of the clip 20, the inner lumen 48 is generally obstructed so that suture lying within the inner lumen 48 will be held fast.

Figure 14A:
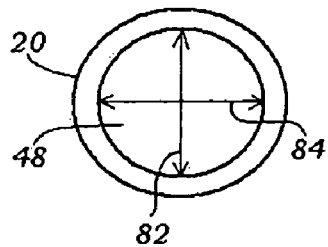
FIGS. 14a and 14b depict end views of a fastener according to a further embodiment of the invention.
Figure 14B:
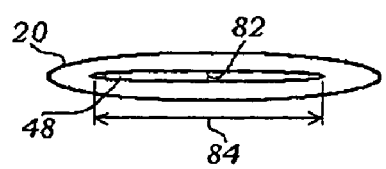

FIGS. 14a and 14b depict a further embodiment of the invention, wherein a clip 20 has no protrusions into the inner lumen 48, but instead relies on varying cross-sectional shapes to obstruct the inner lumen 48. The clip 20 is depicted in FIG. 14a in the open configuration, with the clip 20 having a generally circular-shaped cross section, with the inner lumen 48 having a height 82 generally equal to its width 84. In FIG. 14b the clip 20 is in its closed configuration, with the inner lumen 48 assuming a generally flattened oval shape so that the height 82 and width 84 are no longer generally equal. In the particular embodiment depicted in FIG. 14b, the height 82 is much less than the width 84. Note that the same effect would be achieved by flattening the clip 20 in other directions, e.g., in a side-to-side fashion so that the inner lumen height 82 would be much greater than the width 84. By flattening the clip 20 into a generally flattened oval-shape, the inner lumen 48 is reduced in size so that suture lying therein will be held fast by the clip 20.

Clips according to the invention may be formed from various biocompatible materials, including shape memory and/or pseudoelastic materials such as nitinol. In one embodiment the fastener clip 20 is formed from nitinol (such as an alloy of nickel at 54.5-57% by weight with titanium accounting for the balance except for residual amounts (less than 0.05% each) of oxygen, carbon, and hydrogen) or another shape memory and/or pseudoelastic material, with the fastener clip 20 formed so that the clip engagement tabs 54 extend into the clip inner lumen 48, as depicted in FIG. 4, when in the austenite condition (i.e., when generally unstressed at body temperature). The nitinol can have an austenite finish temperature selected to match the particular application. In a medical suture clip, an austenite finish temperature of −5 degrees to +15 degrees Celsius may be selected.

The fastener clip 20 may be formed from material that will assume its martensite condition when subjected to sufficient stress, such as the stress applied to the clip engagement tabs 54 when the fastener clip 20 is mounted onto the catheter inner body distal end 28, as depicted in FIG. 6a. In such an embodiment, the catheter inner body distal end 28 applies stress to the clip engagement tabs 54, forcing the clip engagement tabs 54 into general alignment with the clip outer wall 46. The stressed material, including the bent material where the clip engagement tabs 54 meet the rest of the clip outer wall 46, is forced into its martensite condition. Then the stress is removed, such as where the fastener clip 20 is removed from the catheter 10 and catheter inner body distal end 28 as depicted in FIGS. 6b and 6c, the material returns to its austenite condition so that the clip engagement tabs 54 are biased inwardly to at least partially block the clip inner lumen 48.

While the invention has been described with reference to particular embodiments, it will be understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. Therefore, it is intended that the invention not be limited to the particular embodiments disclosed herein, but that the invention will include all embodiments falling within the scope of the appended claims.

What is claimed is:

1. A clip for securing suture, the clip comprising:
a generally tubular body having an outer wall and an inner lumen, wherein the generally tubular body is formed from a memory material;
a window cut into the outer wall of the generally tubular body, wherein the window is positioned on a first side of the generally tubular body;
at least one tab cut out from the outer wall of the generally tubular body, wherein the at least one tab is cut out from a second side of the generally tubular body, wherein the second side of the generally tubular body is an opposite side from the first side of the generally tubular body the tab extending across the inner lumen from the first side to the second side so as to at least partially obstruct the inner lumen and to extend at least partially into the window.

2. A clip for securing suture, the clip comprising:
a generally tubular body having an outer wall and an inner lumen;
a window cut into the outer wall of the generally tubular body, wherein the window is positioned on a first side of the generally tubular body;
at least one tab cut out from the outer wall of the generally tubular body, wherein the at least one tab is cut out from a second side of the generally tubular body, wherein the second side of the generally tubular body is an opposite side from the first side of the generally tubular body, the tab extending across the inner lumen from the first side to the second side so as to at least partially obstruct the inner lumen and to extend at least partially into the window, wherein the tab comprises a generally horseshoe shaped portion.

3. A clip for securing suture, the clip comprising:
a generally tubular body having an outer wall and an inner lumen, wherein the inner lumen has a diameter;
a window cut into the outer wall of the generally tubular body, wherein the window is positioned on a first side of the generally tubular body;
at least one tab cut out from the outer wall of the generally tubular body, wherein the at least one tab is cut out from a second side of the generally tubular body, wherein the second side of the generally tubular body is an opposite side from the first side of the generally tubular body, the tab extending across the inner lumen from the first side to the second side so as to at least partially obstruct the inner lumen and to extend at least partially into the window, and wherein the tab comprises a generally elliptical portion, and the generally elliptical portion has a length greater than the inner lumen diameter.

4. A clip for securing suture, the clip comprising:
a generally tubular body having an outer wall and an inner lumen, wherein the inner lumen has a diameter;
a window cut into the outer wall of the generally tubular body, wherein the window is positioned on a first side of the generally tubular body;
at least one tab cut out from the outer wall of the generally tubular body, wherein the at least one tab is cut out from a second side of the generally tubular body, wherein the second side of the generally tubular body is an opposite side from the first side of the generally tubular body, the tab extending across the inner lumen from the first side to the second side so as to at least partially obstruct the inner lumen and to extend at least partially into the window, and wherein the tab comprises a generally elliptical portion, and the generally elliptical portion has a maximum width just less than the inner lumen diameter.

5. A clip for securing suture, the clip comprising:
a generally tubular body having an outer wall and an inner lumen;
a window cut into the outer wall of the generally tubular body, wherein the window is positioned on a first side of the generally tubular body;
at least one tab cut out from the outer wall of the generally tubular body, wherein the at least one tab is cut out from a second side of the generally tubular body, wherein the second side of the generally tubular body is an opposite side from the first side of the generally tubular body, the tab extending across the inner lumen from the first side to the second side so as to at least partially obstruct the inner lumen and to extend at least partially into the window; and
a generally longitudinally-oriented opening in the tab.

6. A system for securing tissue, comprising:
a clip comprising a generally tubular body, an inner lumen, a window cut into a first side of an outer wall of the generally tubular body, and at least one tab cut out from a second side of the generally tubular body and positioned to extend from the second side of the generally tubular body to the first side of the generally tubular body so as to at least partially block the inner lumen and extend at least partially into the window, wherein the first side is an opposite side from the second side; and
a suture line passed through at least one portion of tissue, the suture line comprising first and second suture portions joined by an intermediate suture portion, wherein the first and second suture portions pass through the inner lumen of the clip.

7. The system of claim 6, wherein the at least one tab comprises a generally elliptical portion.

8. The system of claim 7, wherein the clip inner lumen has a diameter, and wherein the generally elliptical portion of the tab comprises a length and a width, and the width is essentially equal to the clip inner lumen diameter.

9. The system of claim 7, wherein the clip inner lumen has a diameter, and wherein the generally elliptical portion of the tab comprises a length and a width, and the length is greater than the clip inner lumen diameter.

10. The system of claim 6, wherein the suture has a diameter that is 20% -40% of the cup inner lumen diameter.

11. The system of claim 10, wherein the suture has a diameter of between 0.006 and 0.008 inches.

12. A method of percutaneously securing suture, comprising:
inserting a suture line percutaneously through a desired portion of a patient's tissue;
providing a clip having an outer wall, an inner lumen, at least one window cut from the outer wall on a first side of the clip, and at least one generally horseshoe-shaped tab cut from the outer wall on a second side of the clip, wherein the first side is an opposite side of the clip from the second side, wherein the clip has an open configuration wherein the tab is generally aligned with the outer wall, and the clip has a closed configuration wherein the tab extends into the inner lumen so as to obstruct most of the inner lumen and to extend from the second side to the first side and at least partially into the window;
positioning the clip in its open configuration on a delivery catheter
threading the suture line through the clip inner lumen;
advancing the clip in its open configuration percutaneously to the desired portion of the patient's tissue; and
transforming the clip from its open configuration to its closed configuration, whereby the suture is secured within the clip.

13. The method of claim 12, wherein transforming the clip from its open configuration to its closed configuration comprises releasing the clip from the delivery catheter.

14. The method of claim 12, wherein the clip comprises a temperature-activated memory material that biases the clip to its closed configuration when exposed to a selected temperature range, and the method further comprises:
exposing the clip to a temperature that biases the clip to its closed configuration.

15. The method of claim 14, wherein providing the clip comprises forming the clip from nitinol.

16. The method of claim 12, wherein providing the clip comprises providing the clip to have the closed configuration wherein the tab extends at least partially into the window without extending outside of the clip.

17. The system of claim 6, wherein the tab is positioned to extend at least partially into the window without extending out of the tubular body.

* * * * *